(12) United States Patent
Smith et al.

(10) Patent No.: US 6,940,411 B2
(45) Date of Patent: Sep. 6, 2005

(54) PERSONAL CARBON MONOXIDE ALARM DEVICE

(75) Inventors: Trevor Smith, Maidstone (GB); Graham Coast, Walderslade (GB)

(73) Assignee: Bedfont Scientific Limited, Rochester (GB)

(*) Notice: Subject to any disclaimer, the term of this patent is extended or adjusted under 35 U.S.C. 154(b) by 117 days.

(21) Appl. No.: 10/358,843

(22) Filed: Feb. 5, 2003

(65) Prior Publication Data

US 2003/0149372 A1 Aug. 7, 2003

(30) Foreign Application Priority Data

Feb. 6, 2002 (GB) .............................................. 0202734

(51) Int. Cl.⁷ .............................................. G08B 17/10
(52) U.S. Cl. ...................... 340/632; 340/691.6; 73/23.3
(58) Field of Search ............................... 340/639, 699.6, 340/693.6, 632, 691.6; 73/233, 23.34, 19.01, 31.05, 23.3

(56) References Cited

U.S. PATENT DOCUMENTS

| | | | | |
|---|---|---|---|---|
| 4,297,689 A | * | 10/1981 | Shaw et al. ................. | 340/632 |
| 5,274,550 A | * | 12/1993 | Greenlee ..................... | 73/23.3 |
| 5,276,434 A | * | 1/1994 | Brooks et al. .............. | 340/632 |
| 5,404,885 A | * | 4/1995 | Sheehan et al. ............ | 600/529 |
| 5,826,577 A | * | 10/1998 | Perroz, Jr. et al. .......... | 600/532 |
| 5,980,934 A | * | 11/1999 | Reber et al. ................ | 424/449 |
| 6,224,897 B1 | * | 5/2001 | Reitberg ..................... | 424/443 |
| 6,305,839 B1 | * | 10/2001 | Krstulovic .................. | 368/281 |
| 6,388,576 B1 | * | 5/2002 | Liu et al. .................... | 340/576 |
| 6,544,190 B1 | * | 4/2003 | Smits et al. ................. | 600/532 |
| 6,599,253 B1 | * | 7/2003 | Baum et al. ................ | 600/532 |

* cited by examiner

*Primary Examiner*—Daniel J. Wu
*Assistant Examiner*—Travis R Hunnings
(74) *Attorney, Agent, or Firm*—Cozen O'Connor; Michael B. Fein; Brian L. Belles

(57) ABSTRACT

A personal alarm device for warning an individual of the presence of an unhealthy amount of carbon monoxide in the blood of the individual, comprising a mouthpiece, a carbon monoxide detector, and an alarm device. The mouthpiece is adapted to detect a minimum predetermined amount of carbon monoxide in the breath and to emit an alarm when the minimum predetermined amount is detected. The personal alarm device is particularly udeful in patient-controlled method of treatment to abate tobacco use.

4 Claims, 1 Drawing Sheet

PERSONAL CARBON MONOXIDE ALARM DEVICE

Figure 1:
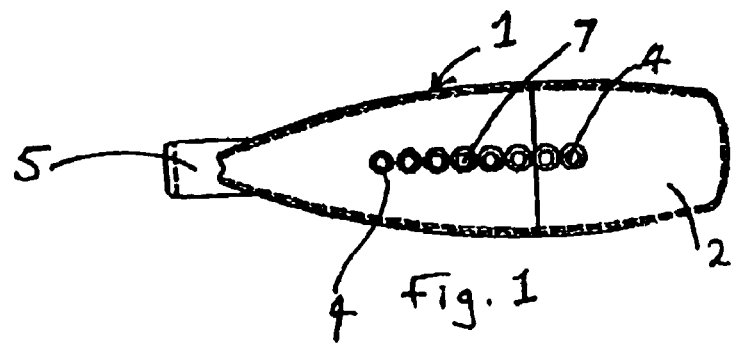

This invention is concerned with a personal alarm device. More particularly, though not exclusively, this invention concerns a personal alarm device suitable for use in a patient-controlled method of treatment to abate tobacco use in humans.

It is known that the presence of high levels of carbon monoxide, present as carboxy-haemoglobin, in the blood can lead to serious health problems in an individual as carbon monoxide reacts with haemoglobin in the blood to form toxic carboxy-haemoglobin. For example, exposure to very high levels of carbon monoxide, such as from a faulty or poorly maintained gas fire, may over a period prove fatal to the individual. An individual who smokes will have significantly higher levels of carboxy-haemaglobin in their blood in comparison to a non-smoker. Over a long period of time, the presence of such high levels of carbon monoxide, along with the other 4000 or more known toxins present in cigarette smoke, may also lead to serious health problems.

Various tobacco abatement programmes to assist individuals to stop or reduce their tobacco consumption are available. For example, individual wishing to stop or reduce smoking may adhere to their skin, as part of their tobacco abatement programme, a patch containing one or more pharmaceutically active materials that, when transmitted transdermally to the individual, aid to reduce cravings in the individual for nicotine. An example of such a patch is disclosed in U.S. Pat. No. 6,224,897.

Devices that can measure with a high degree of accuracy the amount of carbon monoxide exhaled in the breath of an individual have been available for a number of years. An example of such a device is sold by Bedfont Scientific Limited, of Rochester, England, under the trademark SMOKERLYZER®. As the amount of carboxy-haemoglobin in the blood is directly related to the amount of carbon monoxide exhaled in the breath of an individual, health professionals in hospitals and surgeries have used such devices to provide quantitative information concerning the amount of carbon monoxide in the breath of patients as they embark upon and progress in various tobacco abatement programmes: smokers exhale significantly more carbon monoxide in their breath than non-smokers. The devices have been used by health professionals to demonstrate to their patients how successful (or not) their abatement programme has been by comparing the measured amounts of carbon monoxide exhaled from samples of breath taken before and during the abatement programme. If the abatement programme is successful, the patient will be shown by their doctor that the level of carbon monoxide exhaled in their breath reduces as the amount of cigarettes smoked reduces.

Other devices for detecting the content of a chemical in the breath of an individual or in the environment of an individual are known. For example, GB-A-1401056 and U.S. Pat. No. 5,291,898 disclose devices for quantitatively detecting and measuring the content of alcohol on a test subject's breath. However, neither document discloses a device fitted with an alarm. DE-A-1945506 discloses a gas warning and life rescue device, which includes an alarm, that is worn on an individual's wrist. The device is for monitoring the content of a gas in the environment of the individual. None of these documents disclose the use of the devices in a tobacco abatement programme.

Though many individuals in tobacco abatement programmes have used patches successfully, some individuals appear to suffer side effects from possibly excessive use of such patches and/or from concurrent smoking.

As an alternative or supplement to patches, individuals may find it useful, in their tobacco abatement programme, to use a wristwatch comprising a face that indicates permission to smoke or lack of permission to smoke. Such a wristwatch is disclosed in U.S. Pat. No. 6,305,839.

Whether an individual uses patches, a special wristwatch or some other known pharmaceutical means or therapeutic cessation therapy to attempt to reduce or stop their tobacco consumption, there still continues to remain a significant demand for new methods and means for assisting individuals to abate tobacco use.

It is an object of the present invention, therefore, to provide a further means to assist individuals to abate their tobacco use.

Accordingly, in one aspect of the present invention, there is provided a personal alarm device for warning an individual of the presence of a potentially unhealthy amounts of carbon monoxide in the blood of said individual, the device comprising a mouthpiece, a carbon monoxide detector and means for emitting an alarm, wherein the mouthpiece is adapted to receive the breath exhaled by an individual and direct the breath to said detector, wherein said detector is adapted to detect a minimum predetermined amount of carbon monoxide in said breath, and wherein said detector is connected to said means for emitting an alarm such that when said detector detects said predetermined minimum amount or more of carbon monoxide in said breath said means for emitting an alarm emits an alarm.

In one embodiment of the present invention, the means for emitting an alarm comprises a means for emitting a visual alarm, such as one or more light emitting diodes (LEDs) and/or liquid crystal displays (LCDs). In another embodiment, the means for emitting an alarm comprises a means for emitting an audible alarm. In yet another embodiment of the present invention, the means for emitting an alarm comprises both a means for emitting a visual alarm, such as one or more LEDs and/or LCDs, and a means for emitting an audible alarm.

The personal alarm device of the present invention is preferably set to detect, in addition to the predetermined minimum amount, at least one higher amount of carbon monoxide. In this embodiment, the intensity of the alarm emitted by said means for emitting an alarm increases as the detector detects the presence of higher amounts of carbon monoxide in said breath. For example, when the detector is set to detect 10 ppm, 20 ppm, 40 ppm, 60 ppm and 80 ppm of carbon monoxide in of the end tidal breath, the intensity of the alarm emitted increases as the detector detects the increased amount of carbon monoxide in the breath. Such increased intensity may be demonstrated, for example, in the form of 1, 2, 3, 4 or 5 LEDs becoming illuminated, or an LCD changing in colour intensity, or the audible alarm issuing a piercing screech of increasing pitch or bleep frequency, as the detector detects 10 ppm, 20 ppm, 40 ppm, 60 ppm or 80 ppm of carbon monoxide in the end tidal breath, respectively.

In another aspect, the present invention provides an apparatus for use in a patient-controlled method of treatment to abate tobacco use in humans, said apparatus comprising a personal alarm device as described above. Preferably, said apparatus additionally comprises a set of instructions comprising a smoking cessation programme including, as part of the programme, directions for the use of said personal alarm device. Preferably, the programme is set out in hard copy, such as a book or brochure, but it may also be set out in soft copy, such as on floppy disc, video cassette, CD Rom and DVD, or available from an internet web site. Said apparatus may additionally comprise one or more other components such as patches suitable for the transdermal delivery of a pharmaceutically active material useful for suppressing or satisfying a craving for nicotine in said patient, or a wristwatch comprising a face, the face comprising a smoking permission display that indicates either permission to smoke or lack of permission to smoke.

In yet another aspect, the present invention provides the use of a personal alarm device as defined above in a patient-controlled method of treatment to abate tobacco use. The personal alarm device may be used alone or in combination with a specific smoking cessation programme including, as part of the programme, directions for the use of said personal alarm device. Preferably, the programme is set out in hard copy, such as a book or brochure, but it may also be set out in soft copy, such as on floppy disc, video cassette, CD Rom and DVD, or available from an internet web site. One or more other components may also be used in the method, such as an active pharmaceutical, e.g. patches suitable for the transdermal delivery of a pharmaceutically active material useful for suppressing or satisfying a craving for nicotine in said patient, and/or a therapeutic means, e.g. a wristwatch comprising a face, the face comprising a smoking permission display that indicates either permission to smoke or lack of permission to smoke.

The device of the present invention advantageously provides the user with a convenient, qualitative means for determining whether they are being subjected to unhealthy amounts of carbon monoxide, for example through smoking or through exposure to faulty or poorly maintained gas appliances. The present invention may be advantageously employed by an individual to abate their tobacco use. In this respect, it is believed that receipt by an individual of regular visual and/or audible warnings, from the personal alarm device, of the presence of unhealthy amounts of carbon monoxide in their blood can contribute significantly to their success in a tobacco abatement programme.

Figure 3:
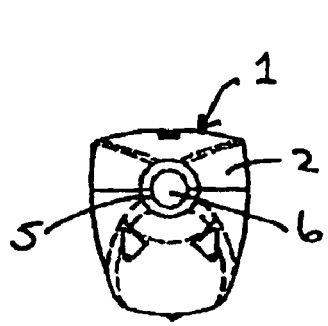
Figure 2:
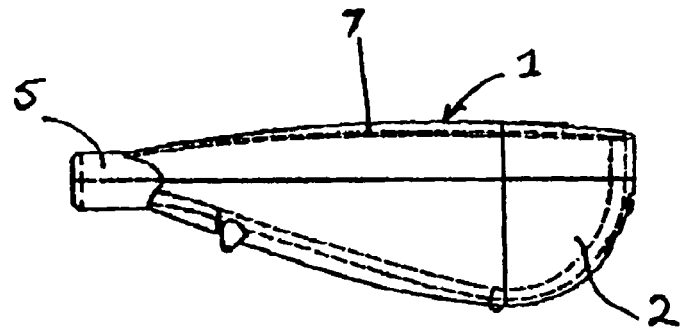
Figure 4:
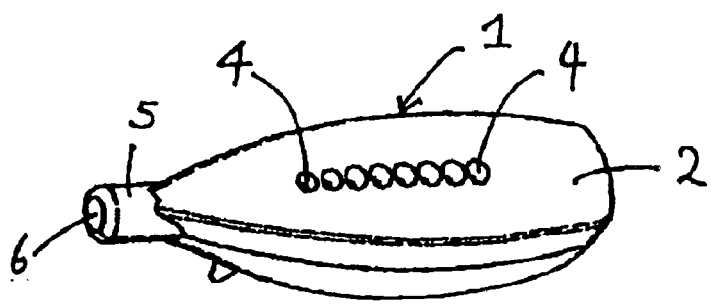

The invention, in some of its various embodiments, shall now be further described with reference to the accompanying drawings in which:

FIG. 1 is a plan view of a personal alarm device in accordance with the present invention, FIG. 2 is a side view of the personal alarm device, FIG. 3 is an end view of the personal alarm device; and FIG. 4 is a perspective view of the personal alarm device Referring now to FIGS. 1 to 4, a personal alarm device 1 of the present invention comprises a body casing 2, which houses a 3v button battery for powering the device, a sampling chamber, an electrochemical sensor and a microprocessor for detecting carbon monoxide in the sampling chamber and controlling output to an LCD and an LCD 7, part of which is visible from outside the body through a series of apertures 4 located in the top of the body. A mouth piece 5, comprises an orifice 6 that leads to the sampling chamber.

In use, once the device is switched on, an individual blows into the mouthpiece 6 of the device, thereby passing breath through the orifice 6 into the sampling chamber. As the breath passes into the sampling chamber it is directed across the face of the electrochemical sensor, where a chemical reaction takes place that produces an electrical output. The electrical output is read by the microprocessor and the results indicated on the LCD, expressed as from 1 to 7 LCD points that may be viewed through 1 to 7 apertures 4 in the body casing 1. A further LCD point, viewed through the eighth aperture, indicates when the power is on.

The device is set such that if the sensor detects a level of carbon monoxide in the breath that is materially above a normal amount typically found in the breath of a non-smoker, then it emits a visible alarm indicated by an LCD point. The more carbon monoxide in the breath, the "louder" the alarm emitted, as indicated by a higher number LCD points.

The device may be used on its own, as a novelty device simply to give a smoker-user a fright, as smokers generally have no idea that they carry high levels of carbon monoxide in their blood. Preferably, however, the alarm is used in a more controlled tobacco abatement programme, where the user receives instructions, such as from a booklet or poster, to use the device at e.g. set times, and how to interpret the different intensities of alarm emitted.

What is claimed is:

1. A patient controlled method of treatment to abate tobacco use, wherein the method comprises the patient exhaling breath into a personal alarm device for warning said individual of the presence of an unhealthy amount of carbon monoxide in the blood of said individual, the device comprising a mouthpiece, a carbon monoxide detector and means for emitting an alarm, wherein the mouthpiece is adapted to receive the breath exhaled by an individual and direct the breath to said detector, wherein said detector is adapted to detect a minimum predetermined amount of carbon monoxide in said breath, and wherein said detector is connected to said means for emitting an alarm such that when said detector detects said predetermined minimum amount or more of carbon monoxide in said breath said means for emitting an alarm emits an alarm, and wherein the detector is set to detect, in addition to the predetermined minimum amount, at least one higher amount of carbon monoxide and wherein the intensity of the alarm emitted by said means for emitting an alarm increases when said detector detects the presence of at least said higher amount (s) of carbon monoxide in said breath.

2. A method as claimed in claim 1, wherein the means for emitting an alarm comprises means for emitting a visual alarm.

3. A method as claimed in claim 2, wherein the means for emitting a visual alarm comprises one or more light emitting diodes and/or one or more liquid crystal displays.

4. A method as claimed in claim 1, wherein the means for emitting an alarm comprises means for emitting an audible alarm.

* * * * *